United States Patent [19]

Walker

[11] Patent Number: 4,533,656

[45] Date of Patent: Aug. 6, 1985

[54] AMIDE DERIVATIVES

[75] Inventor: Edward R. H. Walker, Wilmslow, United Kingdom

[73] Assignee: Imperial Chemical Industries PLC, London, England

[21] Appl. No.: 513,290

[22] Filed: Jul. 13, 1983

[30] Foreign Application Priority Data

Jul. 19, 1982 [GB] United Kingdom ............... 8220879

[51] Int. Cl.$^3$ .................. A61K 37/00; A01N 57/00; A01N 43/42; A01N 43/36; C07D 215/00; C07D 401/00; C07D 211/06

[52] U.S. Cl. ...................... 514/19; 514/278; 514/332; 514/333; 514/354; 514/409; 514/423; 546/16; 546/226; 546/207; 548/408; 548/525; 548/527; 548/526; 548/537

[58] Field of Search ............ 260/112.5 R; 424/258, 424/200, 276; 514/278

[56] References Cited

U.S. PATENT DOCUMENTS

| | | | |
|---|---|---|---|
| 4,296,110 | 10/1981 | Johnson | 424/274 |
| 4,303,583 | 12/1981 | Kim et al. | 424/200 |
| 4,344,949 | 8/1982 | Hoefle et al. | 424/258 |
| 4,374,829 | 2/1983 | Harris et al. | 260/112.5 R |

FOREIGN PATENT DOCUMENTS 2502614  1/1982  France ............ 260/112.5 R

Primary Examiner—Delbert R. Phillips
Attorney, Agent, or Firm—Cushman, Darby & Cushman

[57] ABSTRACT

Amide derivatives of the formula:

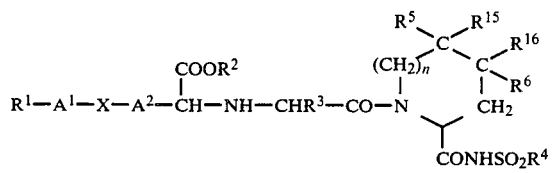

wherein either $R^1$ is aryl or heterocyclic and $A^1$ is a direct link, or $R^1$ is aryl or heterocyclic, or hydrogen or amino and $A^1$ is alkylene; X is —$CH_2$— or —CO— or has the formula

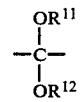

wherein $R^{11}$ and $R^{12}$, which may be the same or different, each is alkyl, or $R^{11}$ and $R^{12}$ are joined to form alkylene; $A^2$ is alkylene; $R^2$ is hydrogen, aryl or alkyl which is unsubstituted or which bears an aryl substituent; $R^3$ is hydrogen or alkyl which is unsubstituted or which bears a halogeno, hydroxy, amino, guanidino, carboxy, carbamoyl, mercapto, alkoxy, alkylamino, dialkylamino, cyclic amino, alkylthio, alkanoylamino, alkoxycarbonyl, arylalkoxycarbonyl, aryl or heterocyclyl substituent; $R^4$ is alkyl which is unsubstituted or which bears an aryl substituent, or $R^4$ is phenyl or alkylphenyl; n is 0 or 1; and either $R^5$, $R^6$, $R^{15}$ and $R^{16}$ are all hydrogen, or $R^5$ and $R^6$ are both hydrogen and $R^{15}$ and $R^{16}$ together form tetramethylene; or $R^5$ and $R^6$ together form a second bond between the two carbon atoms to which they are attached and $R^{15}$ and $R^{16}$ together form buta-1,3-dien-1,4-diyl; or a salt thereof; processes for their manufacture and pharmaceutical compositions containing them. The compounds are inhibitors of angiotensin converting enzyme.

7 Claims, No Drawings

AMIDE DERIVATIVES

This invention relates to new amide derivatives and more particularly it relates to amide derivatives which are inhibitors of angiotensin converting enzyme (ACE).

European Patent Specification No. 12401 describes ACE inhibitors of the general formula:

$$RCOCR^1R^2NHCHR^3CONR^4CR^5R^7COR^6$$

wherein the various R groups are defined in said specification. One compound which is described therein is at an advanced stage of clinical trial. This compound is known as MK 421 or enalapril and has the chemical structure:

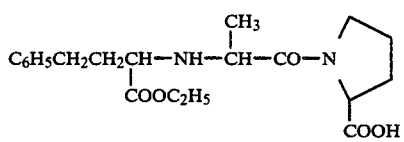

In our copending European Patent Application No. 83300169 and also in European Patent Specification No. 48159 in the name of the University of Miami, there are described ACE inhibitors related to enalapril wherein there is present a carbonyl group in the phenylethyl part of the structure.

The only sulphonamides of amino acids of which we are aware are sulphonamides of racemic phenylalanine and related compounds which are described in Monatshefte fur Chemie, 1968, 99, 1289-1319. No pharmacological properties are described for said sulphonamides.

We have now discovered that sulphonamide derivatives of the proline part both of enalapril and of the carbonyl derivatives thereof are particularly valuable ACE inhibitors, especially because of their oral activity.

According to the present invention there is provided an amide derivative of the formula:

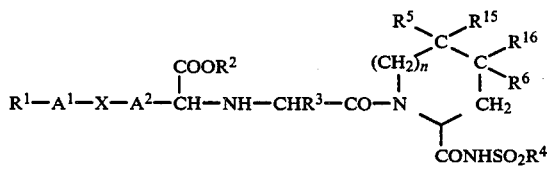

wherein either $R^1$ is aryl or heterocyclic and $A^1$ is a direct link, or $R^1$ is aryl or heterocyclic, or hydrogen or amino and $A^1$ is alkylene of 1 to 5 carbon atoms; wherein X is —$CH_2$— or —CO— or has the formula

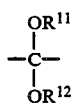

wherein $R^{11}$ and $R^{12}$, which may be the same or different, each is alkyl of up to 5 carbon atoms, or $R^{11}$ and $R^{12}$ are joined to form alkylene of 2 to 5 carbon atoms; wherein $A^2$ is alkylene of 1 to 4 carbon atoms; wherein $R^2$ is hydrogen, aryl or alkyl of up to 5 carbon atoms which is unsubstituted or which bears an aryl substituent; wherein $R^3$ is hydrogen or alkyl of up to 5 carbon atoms which is unsubstituted or which bears a halogeno, hydroxy, amino, guanidino, carboxy, carbamoyl or mercapto substituent, or an alkoxy, alkylamino, dialkylamino, cyclic amino or alkylthio substituent wherein each alkyl is of up to 5 carbon atoms and wherein cyclic amino has up to 6 carbon atoms, or an alkanoylamino or alkoxycarbonyl substituent each of up to 6 carbon atoms or an arylalkoxycarbonyl substituent of up to 10 carbon atoms, or an aryl or heterocyclyl substituent; wherein $R^4$ is alkyl of up to 5 carbon atoms which is unsubstituted or which bears an aryl substituent, or $R^4$ is phenyl or alkylphenyl; wherein n is 0 or 1; and wherein either $R^5$, $R^6$, $R^{15}$ and $R^{16}$ are all hydrogen, or $R^5$ and $R^6$ are both hydrogen and $R^{15}$ and $R^{16}$ together form tetramethylene [—$(CH_2)_4$—]; or $R^5$ and $R^6$ together form a second bond between the two carbon atoms to which they are attached and $R^{15}$ and $R^{16}$ together form buta-1,3-dien-1,4-diyl such that together with the $CR^5$-$CR^6$ group they form a fused benzo-ring; or a salt thereof where appropriate.

It will be observed that there are various potentially asymmetrical carbon atoms in the amide of the invention, in particular the carbon atom which bears the substituent —$COOR^2$, the carbon atom which bears the substituent —$R^3$ when this substituent is other than hydrogen, and the carbon atom which bears the substituent —$CONHOS_2R^4$, and that the amide may therefore exist in racemic and optically active forms. It is to be understood that this invention encompasses the racemic form and any optically-active form which possesses ACE-inhibiting properties, it being a matter of common general knowledge how an optically active compound may be prepared and how the ACE-inhibiting properties of a compound may be measured.

A suitable value for $R^1$ or $R^2$ when it is aryl, or for the aryl substituent in the group $R^2$, $R^3$ or $R^4$ when said group is alkyl substituted by aryl is, for example, unsubstituted phenyl or naphthyl, or phenyl or naphthyl substituted by one or more substituents selected from halogen, for example fluorine, chlorine, bromine and iodine, alkyl and alkoxy each of up to 5 carbon atoms, for example methyl, ethyl, t-butyl, methoxy and ethoxy and hydroxy, amino, carboxy, carbamoyl and trifluoromethyl, and aryl, for example phenyl and p-chlorophenyl, and substituents of the formula:

wherein either $R^{30}$ and $R^{31}$, which may be the same of different, each is alkyl of up to 5 carbon atoms, for example methyl, ethyl or n-propyl, which is unsubstituted or which is substituted by phenyl, or $R^{30}$ and $R^{31}$ are joined such that together with the adjacent nitrogen atom they form pyrrolidino, carboxypyrrolidino, alkoxycarbonylpyrrolidino, piperidino, 4-methylpiperazino or morpholino, and wherein -alk- is alkylene of 1 to 4 carbon atoms.

A suitable value for $R^1$ when it is heterocyclic, or for the heterocyclyl substituent in $R^3$ when it is alkyl substituted by heterocyclic, is, for example, a 5- or 6-membered heterocyclic ring containing 1 or 2 heteroatoms selected from oxygen, nitrogen and sulphur, which ring may be saturated or unsaturated, which ring may be single or may be fused to a benzene ring, and which ring may optionally contain one or more oxo, alkyl or halogeno substituents, for example methyl, chloro or bromo substituents. Suitable heterocyclic rings are, for example, pyridyl, furyl, 5-methyl-2-furyl, thienyl, imidazolyl, thiazolyl, isoxazolyl, indolyl, benzofuryl, benzothienyl, quinolyl, 1-methyl-1,2,3,4-tetrahydroquinol-6-yl, benzimidazolyl, 1,3-benzodioxol-5-yl or 1,4-benzodioxan-6-yl.

A suitable value for alkylene formed by $R^{11}$ and $R^{12}$ joined together is, for example, ethylene, trimethylene or 2,2-dimethyltrimethylene.

A suitable value for $A^2$ or for $A^1$ when it is alkylene, is, for example, methylene, ethylene, trimethylene, ethylidene (—CHCH$_3$—), 1-methylethylidene [—C(CH$_3$)$_2$—], 1-methylethylene, 2-methylethylene or 2,2-dimethylethylene.

A suitable value for $R^2$, $R^3$, $R^4$, $R^{11}$, or $R^{12}$ when it is alkyl is, for example, methyl, ethyl, n-propyl, isopropyl, n-butyl, isobutyl or t-butyl.

A suitable value for the halogeno substituent in $R^3$ is, for example, fluoro or chloro.

A suitable value for the alkoxy substituent in $R^3$ when it is alkyl substituted by alkoxy is, for example, methoxy, ethoxy, n-propoxy, isopropoxy, n-butoxy or t-butoxy.

A suitable value for the alkylamino, dialkylamino or cyclic amino substituent in $R^3$ wherein it is alkyl bearing such a substituent is, for example, methylamino, ethylamino, dimethylamino, pyrrolidino, piperidino, 4-methylpiperazino or morpholino.

A suitable value for the alkylthio, alkanoylamino, alkoxycarbonyl or arylalkoxycarbonyl substituent in $R^3$ when it is alkyl substituted by alkylthio, alkanoylamino, alkoxycarbonyl or arylalkoxycarbonyl is, for example, methylthio, acetamido, methoxycarbonyl or benzyloxycarbonyl.

A suitable value for $R^4$ when it is alkylphenyl is, for example, p-tolyl.

Preferably $R^1$ is phenyl, p-methoxyphenyl, 2-thienyl or benzo[b]fur-2-yl, $A^1$ is a direct link, X is —CH$_2$— or —CO— or 2,2-dimethyltrimethylene-1,3-dioxymethylene, $A^2$ is methylene, ethylene or trimethylene, $R^2$ is hydrogen, alkyl of up to 5 carbon atoms, especially methyl, ethyl, isopropyl, n-butyl or t-butyl, or benzyl, $R^3$ is methyl, 4-aminobutyl, 2-carboxyethyl or 2-alkoxycarbonylethyl and the stereochemistry of —CHR$^3$— is that derived from L-alanine, L-lysine or L-glutamic acid respectively, n is 0, $R^5$, $R^6$, $R^{15}$ and $R^{16}$ are all hydrogen and $R^4$ is phenyl or alkyl of up to 5 carbon atoms which is unsubstituted or which bears a phenyl substituent, especially methyl, ethyl, n-propyl, isopropyl, n-butyl, isobutyl, benzyl or 3-phenylpropyl.

A particularly preferred amide derivative of the invention has the formula stated above wherein $R^1$ is phenyl, p-methoxyphenyl, 2-thienyl or benzo[b]fur-2-yl, $A^1$ is a direct link, X is —CH$_2$— or —CO— or 2,2-dimethyltrimethylene-1,3-dioxymethylene, $A^2$ is methylene, ethylene or trimethylene, $R^2$ is hydrogen or alkyl of up to 5 carbon atoms, $R^3$ is methyl (such that —CHR$^3$— is derived from L-alanine), n is 0, $R^5$, $R^6$, $R^{15}$ and $R^{16}$ are all hydrogen and $R^4$ is alkyl of up to 5 carbon atoms.

A suitable salt of an amide derivative of the invention wherein $R^2$ is hydroxy is, for example, an alkali metal or alkaline earth metal salt, for example a sodium, potassium, calcium or magnesium salt, or an ammonium or dicyclohexylamine salt.

Specific compounds of the invention are hereinafter described in the Examples. Of these, a preferred compound is N-(1-carboxy-3-phenylpropyl)-L-alanyl-L-proline ethanesulphonamide or a salt thereof or the ethyl ester thereof.

An amide derivative of the invention may be manufactured by any chemical process known to be suitable for preparing compounds of related chemical types.

A preferred process for the manufacture of an amide derivative of the invention wherein X is —CH$_2$— or —C(OR$^{11}$)(OR$^{12}$)— comprises the reaction of a compound of the formula:

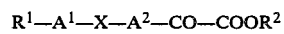

wherein $R^1$, $A^1$, X, $A^2$ and $R^2$ have the meanings stated above, with a compound of the formula:

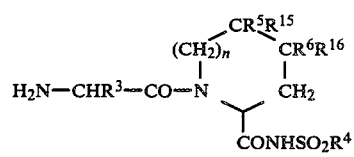

wherein $R^3$, $R^4$, $R^5$, $R^6$, $R^{15}$, $R^{16}$ and n have the meanings stated above, under reducing conditions.

The reaction may be carried out in an alcoholic solvent, for example ethanol, and the reducing conditions are suitably provided by sodium cyanoborohydride or by Raney nickel.

Alternatively, an amide derivative of the invention wherein X is —CH$_2$— or —C(OR$^{11}$)(OR$^{12}$)— may be obtained by the reaction of a compound of the formula:

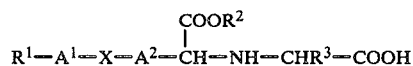

wherein $R^1$, $A^1$, X, $A^2$, $R^2$ and $R^3$ have the meanings stated above, with a compound of the formula:

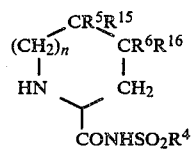

wherein $R^4$, $R^5$, $R^6$, $R^{15}$ and $R^{16}$ have the meanings stated above.

The last mentioned reaction may be carried out in the presence of a condensing agent, for example a carbodiimide. The starting material for the last-mentioned process may be obtained by the reaction of a compound of the formula:

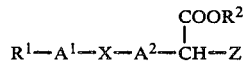

wherein $R^1$, $A^1$, X, $A^2$ and $R^2$ have the meanings stated above and wherein Z is a displaceable radical, for example the bromine atom, with a compound of the formula H$_2$NCHR$^3$COOR, wherein R is an easily removable protecting group, for example the t-butyl group.

A preferred process for the manufacture of an amide derivative of the invention wherein X is —CO— and $A^2$ is methylene comprises the reaction of a compound of the formula:

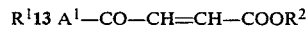

wherein $R^1$, $A^1$ and $R^2$ have the meanings stated above, with a compound of the formula:

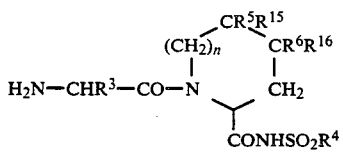

wherein $R^3$, $R^4$, $R^5$, $R^6$, $R^{15}$, $R^{16}$ and n have the meanings stated above.

The reaction may be carried out in an inert diluent or solvent, for example dichloromethane, ethylene dichloride or dimethylformamide, and it is preferably carried out at laboratory temperature.

An amide derivative of the invention wherein $R^2$ is other than hydrogen may be obtained from the corresponding acid wherein $R^2$ is hydrogen by conventional means of ester formation.

An amide derivative of the invention wherein $R^2$ is hydrogen may be obtained by the hydrolysis of the corresponding amide derivative wherein $R^2$ is alkyl, or, when $R^2$ is t-butyl, by the acid-catalysed cleavage of said compound, or, when $R^2$ is benzyl, by the catalytic hydrogenolysis of said compound.

An amide derivative of the invention wherein X has the formula $-C(OR^{11})(OR^{12})-$ may be converted into the corresponding amide derivative of the invention wherein X is $-CO-$ by acid hydrolysis.

As stated above, an amide derivative of the invention possesses ACE-inhibiting properties. ACE is the enzyme which converts angiotensin I to angiotensin II. The ACE-inhibiting properties of an amide derivative of the invention may be demonstrated by its ability to prevent the cleavage of angiotensin I or of a synthetic peptide related to angiotensin I by ACE.

Angiotensin II is a potent constrictor of vascular smooth muscle, and is therefore involved in the control of blood pressure. A compound which prevents conversion of angiotensin I to angiotensin II will therefore lower circulating levels of angiotensin II and cause a fall in blood pressure. An amide derivative of the invention may therefore be used in conditions in which known ACE-inhibitors are used, for example to lower blood pressure or to treat congestive heart failure in a warm-blooded animal (including a human). At a dose of an amide derivative of the invention which lowers blood pressure in an experimental animal, for example a rat, no symptoms of toxicity are apparent.

An amide derivative of the invention may be administered to a warm-blooded animal, including man, in the form of a pharmaceutical composition comprising as active ingredient at least one amide derivative of the invention, or a salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the amide derivative of the invention, one or more drugs selected from diuretics, for example bendrofluazide, chlorothiazide and chlorthalidone; and other hypotensive agents, for example β-adrenergic blocking agents, for example atenolol and propranolol.

When used for the treatment of hypertension or congestive heart failure in man, it is expected that the amide derivative of the invention would be given to man at a total oral dose of between 1 mg. and 500 mg. daily, at doses spaced at 6–8 hourly or longer intervals, or at an intravenous dose of between 0.1 mg. and 50 mg.

Preferred oral dosage forms are tablets or capsules containing between 1 mg. and 100 mg. of active ingredient. Preferred intravenous dosage forms are sterile aqueous solutions of active ingredient containing between 0.1% and 1% w/v of active ingredient.

The invention is illustrated but not limited by the following Examples:

EXAMPLE 1

Powdered activated 4 Å molecular sieve (12.5 g.) followed by triethylamine (1.0 ml.) were added to a stirred solution of L-alanyl-L-proline methanesulphonamide trifluoroacetate (2.77 g.) in ethanol (40 ml.). Ethyl 2-oxo-4-phenylbutyrate (8.3 g.) was then added and the mixture was stirred at laboratory temperature for 30 minutes. A solution of sodium cyanoborohydride (0.7 g.) in ethanol (30 ml.) was then added during 6 hours and the mixture was stirred for a further 10 hours, filtered through a filter-aid and the filtrate was evaporated to dryness under reduced pressure. The residue was partitioned between saturated aqueous sodium carbonate solution (100 ml.) and diethyl ether (100 ml.) and the aqueous layer was separated, acidified to pH 3 with concentrated aqueous hydrochloric acid and extracted with methylene chloride. The extract was dried and evaporated to dryness under reduced pressure and the residue was purified by chromatography on a silica gel column using a 9:1 v/v mixture of methylene chloride and methanol as eluant. There was thus obtained N-(1-ethoxycarbonyl-3-phenylpropyl)-L-alanyl-L-proline methanesulphonamide hemihydrate as a foam, the structure of which was confirmed by proton magnetic resonance spectroscopy and by elemental analysis (Found: C, 54.5%; H, 6.9%; N, 9.1% $C_{21}H_{31}N_3O_6S,\frac{1}{2}$ $H_2O$ requires C,54.8% H, 6.9% N,9.1%).

The L-alanyl-L-proline methanesulphonamide trifluoroacetate used as starting material was obtained as follows:

A mixture of N-t-butoxycarbonyl-L-alanyl-L-proline benzyl ester (3.76 g.), a 10% palladium-on-charcoal catalyst (0.5 g.) and ethanol (50 ml.) was shaken with hydrogen at laboratory temperature and pressure for 16 hours and then filtered, and the filtrate was evaporated to dryness under reduced pressure.

A solution of N, N'-dicyclohexylcarbodiimide (2.88 g.) in methylene chloride (20 ml.) was added to a stirred solution of the N-t-butoxycarbonyl-L-alanyl-L-proline thus obtained (4.0 g.), methanesulphonamide (1.33 g.) and 4-dimethylaminopyridine (1.71 g.) in methylene chloride which was maintained under an inert atmosphere, and the mixture was stirred at laboratory temperature for 16 hours and then filtered. The filtrate was evaporated to dryness, the residue was dissolved in ethyl acetate and the mixture was filtered again. The filtrate was evaporated to dryness and the residue was partitioned between saturated aqueous sodium carbonate solution (150 ml.) and diethyl ether (150 ml.). The aqueous layer was separated, acidified to pH3 with concentrated aqueous hydrochloric acid and extracted three times with ethyl acetate (100 ml. each time). The combined extracts were dried and evaporated to dryness under reduced pressure.

A mixture of the N-butoxycarbonyl-L-alanyl-L-proline methanesulphonamide thus obtained (1.86 g.) and trifluoroacetic acid (15 ml.) was stirred under an inert atmosphere at laboratory temperature for 1 hour and then evaporated to dryness under reduced pressure. There was thus obtained L-alanyl-L-proline methanesulphonamide trifluoroacetate which was used without further purification.

EXAMPLE 2

Powdered activated 4 Å molecular sieve (13.5 g.) followed by triethylamine (11.13 ml.) were added to a stirred solution of L-alanyl-L-proline ethanesulphonamide trifluoroacetate (31.1 g.) in ethanol (450 ml.). Ethyl 2-oxo-4-phenylbutyrate (41.0 g.) was then added and the mixture was stirred at laboratory temperature for 30 minutes. A solution of sodium cyanoborohydride (7.7 g.) in ethanol (225 ml.) was then added during 15 hours and the mixture was stirred for a further 10 hours, filtered through a filter-aid and the filtrate was evaporated to dryness under reduced pressure. The residue was partitioned between saturated aqueous sodium carbonate solution (1000 ml.) and diethyl ether (1000 ml.) and the aqueous layer was separated, acidified to pH 3 with concentrated aqueous hydrochloric acid and extracted with methylene chloride. The extract was dried and evaporated to dryness under reduced pressure and the residue was purified by chromatography on a silica gel column using a 9:1 v/v mixture of methylene chloride and methanol as eluant. There were thus obtained the mixed isomers of N-(1-ethoxycarbonyl-3-phenylpropyl)-L-alanyl-L-proline ethanesulphonamide in a ratio (as shown by high pressure liquid chromatography) of approximately 11:9 by weight. The isomers were separated by chromatography on a silica gel column using a 99:1 v/v mixture of ethyl acetate and acetic acid as eluant, and there were thus separately obtained N-[(1R)-1-ethoxycarbonyl-3-phenylpropyl]-L-alanyl-L-proline ethanesulphonamide, and N-[(1S)-1-ethoxycarbonyl-3-phenylpropyl]-L-alanyl-L-proline ethanesulphonamide, both of which were oils, the structures of which were confirmed by proton magnetic resonance and mass spectroscopy. The isomer initially present as 45% by weight of the mixture was considerably more active as an inhibitor of ACE than the other isomer.

A saturated solution of hydrogen chloride in ethyl acetate (3 ml.) was added to a solution of the more active (as an inhibitor of ACE) isomer described above (0.3 g.) in ethyl acetate (3 ml.) and the mixture was cooled to −20° C. and then filtered. There was thus obtained as solid residue N-[(1R or S)-1-ethoxycarbonyl-3-phenylpropyl]-L-alanyl-L-proline ethanesulphonamide, m.p. 110°–120° C.

The L-alanyl-L-proline ethanesulphonamide trifluoroacetate used as starting material was obtained by a similar process to that described in the second part of Example 1 except that ethanesulphonamide was used in place of methanesulphonamide.

EXAMPLE 3

A mixture of N-t-butoxycarbonyl-L-alanyl-L-proline ethanesulphonamide (22.5 g.) and trifluoroacetic acid (60 ml.) was stirred at laboratory temperature for 1 hour, the excess of trifluoroacetic acid was removed by evaporation and toluene was twice added and removed by evaporation, finally at 0.5 mm.Hg. A solution of the L-alanyl-L-proline ethanesulphonamide trifluoroacetate thus obtained in ethanol (350 ml.) was cooled to 10° C. and triethylamine (17 ml.), a solution of ethyl 2-oxo-4-phenylbutyrate (18.6 g.) in ethanol (50 ml.), powdered activated 3 Å molecular sieve (75 g.) and Raney nickel (15 g.) were successively added. The mixture was stirred under an atmosphere of hydrogen at laboratory temperature and pressure for 20 hours and then filtered through a filter-aid, and the filtrate was evaporated to dryness. The residue was shaken with diethyl ether and 10% aqueous potassium carbonate solution and the aqueous layer was separated, washed with diethyl ether, acidified to pH 3 with citric acid and extracted four times with ethyl acetate. The combined extracts were dried and evaporated to dryness and there were thus obtained the mixed isomers of N-(1-ethoxycarbonyl-3-phenylpropyl)-L-alanyl-L-proline ethanesulphonamide in a ratio (as shown by high pressure liquid chromatography) of approximately 22:3 by weight, the more active (as an inhibitor of ACE) isomer predominating.

Maleic acid (5.2 g.) was added to a solution of the mixed isomers thus obtained in acetonitrile (50 ml.), diethyl ether (100 ml.) was added and the mixture was kept at 4° C. for 16 hours and then filtered. The solid product was crystallised from a mixture of acetonitrile and diethyl ether and there was thus obtained the single isomer N-[(1R or S)-1-ethoxycarbonyl-3-phenylpropyl]-L-alanyl-L-proline ethanesulphonamide maleate, m.p. 85°–95° C., $[\alpha]_D^{22} = -46.4°$ (C, 1% in ethanol). This was the more active (as an inhibitor of ACE) isomer.

Elemental Analysis: Found, C:52.5%, H:6.4%, N:7.0%, S:5.4% $C_{26}H_{37}N_3O_{10}S$. $\frac{1}{2}H_2O$ requires C:52.7%, H:6.5%, N:7.1%, S:5.4%.

Proton Magnetic Resonance Spectrum (in hexadeutero-dimethylsulphoxide and tetradeuteroacetic acid at 25° C.)

| Shift (δ) | Type of Peak | No of H Atoms | Specific H Atoms |
| --- | --- | --- | --- |
| 7.3 | multiplet | 2 ⎱ | |
| 7.2 | multiplet | 3 ⎰ | 1 |
| 6.1 | singlet | 2 | 15, 16 |
| 4.4 | multiplet | 1 | 12 |
| 4.1–4.2 | multiplet | 2 | 5 |
| 3.95 | multiplet | 1 | 4 |
| 3.45–3.65 | multiplet | 3 | 7, 9 |
| 3.3 | quartet | 2 | 13 |
| 2.7 | multiplet | 1 ⎱ | |
| 2.6 | multiplet | 1 ⎰ | 2 |
| 1.8–2.2 | multiplet | 6 | 3, 10, 11 |
| 1.3 | doublet | 3 | 8 |
| 1.2 | multiplet | 6 | 6, 14 |

Mass Spectrum

| Mass No | Ion |
| --- | --- |
| 468 | $(M + H)^{\oplus}$ |
| 394 | $M-COOC_2H_5$ |
| 359 | |
| 313 | $359 - C_2H_5OH$ |

| Mass No | Ion |
|---|---|
| 254 | 359 - $C_6H_5CH_2CH_2$ |
| | $COOC_2H_5$ |

$$C_6H_5CH_2CH_2CH-NH=CH-CH_3 \quad \oplus$$

The N-t-butoxycarbonyl-L-alanyl-L-proline ethanesulphonamide used as starting material was obtained as follows:

A solution of dicyclohexylcarbodiimide (103 g.) in methylene chloride (250 ml.) was added to a stirred solution of N-t-butoxycarbonyl-L-proline (101 g.), ethanesulphonamide (54.5 g.) and 4-dimethylaminopyridine (61 g.) in methylene chloride (2500 ml.) which was cooled to 0° C., and the mixture was allowed to warm up to laboratory temperature, stirred at that temperature for 4 days and then filtered. The filtrate was evaporated to dryness and the residue was partitioned between diethyl ether (1000 ml.) and saturated sodium bicarbonate solution (1000 ml.). The aqueous solution was separated, neutralised with concentrated aqueous hydrochloric acid, acidified with citric acid and extracted with ethyl acetate. The extract was dried and evaporated to dryness, the residue was stirred with diethyl ether and the mixture was filtered. There was thus obtained as solid product N-t-butoxycarbonyl-L-proline ethanesulphonamide, m.p. 170°–172° C.

A mixture of the above sulphonamide (78.4 g.) and trifluoroacetic acid (100 ml.) was stirred at laboratory temperature for 150 minutes, the excess of trifluoroacetic acid was removed by evaporation and toluene was twice added and removed by evaporation. The residue was dissolved in dimethylformamide (1250 ml.), the solution was stirred and cooled to 0° C. and triethylamine was added until the pH was between 6 and 7. N-t-Butoxycarbonyl-L-alanine 2, 4, 5-trichlorophenyl ester (105 g.) was added and the mixture was stirred at 0° C. for 4 hours and then at laboratory temperature for 2 days, and then poured into ice-water (2000 ml.). The mixture was acidified to pH5 with citric acid and extracted with ethyl acetate and the extract was dried and evaporated to dryness. The residue was partitioned between diethyl ether and aqueous sodium bicarbonate solution and the aqueous layer was separated, acidified to pH 3 with citric acid and extracted with ethyl acetate. The extract was dried and evaporated to dryness and there was thus obtained as solid residue N-t-butoxycarbonyl-L-alanyl-L-proline ethanesulphonamide, m.p. 93°–97° C.

EXAMPLE 4

The process described in Example 1 was repeated using the appropriate alkyl 2-oxoalkanoate and the appropriate L-alanyl-L-proline sulphonamide trifluoroacetate as starting materials, and there were thus obtained the compounds shown in the following table:

$$R^1-X-A^2-\overset{COOR^2}{\underset{|}{CH}}-NH-\overset{CH_3}{\underset{|}{CH}}-CO-N\overset{\diagup}{\diagdown}$$
$$CONHSO_2R^4$$

| $R^1$ | X | $A^2$ | $R^2$ | $R^4$ | Note |
|---|---|---|---|---|---|
| phenyl | $CH_2$ | $CH_2$ | ethyl | n-propyl | 1(1%) |
| phenyl | $CH_2$ | $CH_2$ | ethyl | isopropyl | 1(1%) |
| phenyl | $CH_2$ | $CH_2$ | ethyl | n-butyl | 1(1%) |
| phenyl | $CH_2$ | $CH_2$ | ethyl | isobutyl | |
| phenyl | $CH_2$ | $CH_2$ | ethyl | phenyl | 1(1%) |
| phenyl | $CH_2$ | $CH_2$ | ethyl | benzyl | 1(1%) |
| phenyl | $CH_2$ | $CH_2$ | ethyl | 3-phenyl-propyl | 1(1%) |
| phenyl | $CH_2$ | $CH_2$ | methyl | ethyl | |
| phenyl | $CH_2$ | $CH_2$ | t-butyl | ethyl | |
| phenyl | $CH_2$ | $(CH_2)_2$ | ethyl | methyl | |
| phenyl | $CH_2$ | $(CH_2)_3$ | ethyl | methyl | |
| p-methoxyphenyl | $CH_2$ | $CH_2$ | ethyl | methyl | |
| 2-thienyl | $CH_2$ | $CH_2$ | ethyl | methyl | |
| isopropyl | $CH_2$ | $CH_2$ | benzyl | ethyl | 3 |
| phenyl | $X^1$ | $(CH_2)_3$ | ethyl | methyl | 2, 4 |
| 2-thienyl | $X^1$ | $(CH_2)_3$ | ethyl | ethyl | 1(3%), 2, 5 |
| benzo[b]fur-2-yl | $X^1$ | $(CH_2)_3$ | ethyl | ethyl | 2, 6 |
| 2-thienyl | CO | $(CH_2)_3$ | ethyl | ethyl | 7 |
| benzo[b]fur-2-yl | CO | $(CH_2)_3$ | ethyl | ethyl | 8 |

Note 1 Isomers were separated as described in Example 2 by chromatography on a silica gel column using the indicated percentage by volume of acetic acid in ethyl acetate as eluant.

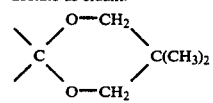

Note 2 $X^1$ is the group

Notes 3, 4, 5 and 6 relate to preparation of starting materials as described below.

Note 7 Hydrochloride salt prepared from 0.29 g. of each separate isomer of the corresponding compound wherein X is $X^1$ by stirring with 2N-hydrogen chloride in acetic acid (5 ml.) at laboratory temperature for 2 hours and then evaporating to dryness.

Note 8 Trifluoroacetate salt prepared from 0.25 g. of the compound wherein X is $X^1$ by stirring with 90% aqueous trifluoroacetic acid (3 ml.) at laboratory temperature for 4.5 hours and then evaporating to dryness.

Preparation of Starting Materials

A. The L-alanyl-L-proline sulphonamides used as starting materials were obtained by a similar process to that described in the second part of Example 1 using the appropriate sulphonamide in place of methanesulphonamide.

Isobutylsulphonamide was prepared as follows:

A solution of sodium chlorate (25 g.) in saturated aqueous sodium bicarbonate solution (70 ml.) was added to a stirred mixture of isobutanethiol (19.2 ml.), acetic acid (150 ml.) and concentrated aqueous hydrochloric acid (50 ml.) which was cooled to −10° C., and the mixture was stirred for 1 hour below 0° C. and then filtered. The filtrate was extracted four times with ethyl acetate (200 ml. each time) and the combined extracts were washed with saturated aqueous sodium bicarbonate solution, dried and evaporated to dryness. Ammonia was passed through a stirred solution of the isobutylsulphonyl chloride thus obtained (20.08 g.) in toluene (200 ml.) which was cooled to −20° C. until no further ammonia was absorbed. The mixture was filtered, the filtrate was evaporated to dryness and the residue was purified by chromatography on silica gel column using initially toluene, and then a 9:1 v/v mixture of methylene chloride and methanol, as eluant. There was thus obtained isobutylsulphonamide as an oil.

B. The alkyl 2-oxo-4-phenylbutyrates were obtained by esterification of 2-oxo-4-phenylbutyric acid by conventional means. The methyl ester was prepared using diazomethane, and the t-butyl ester was prepared by reacting the acid with isobutylene in methylene chloride solution in the presence of a catalytic amount of concentrated sulphuric acid.

C. The ethyl 2-oxoalkanoates used as starting materials wherein X is —CH$_2$— were in general obtained by the reaction of the Grignard reagent of the formula R$^1$—X—A$^2$—MgBr with diethyl oxalate. However, the starting material wherein R$^1$ is isopropyl, and the starting materials wherein X is X$^1$, were obtained as individually described below.

Benzyl 5-methyl-2-oxohexanoate (Note 3)

A solution of 5-methyl-2-oxohexanoic acid (0.288 g.) in methylene chloride (1 ml.) was added during 15 minutes to a stirred solution of dicyclohexylcarbodiimide (0.412 g.) and benzyl alcohol (0.432 g.) in methylene chloride (10 ml.) which was cooled to −15° C., and the mixture was stirred at that temperature for 1 hour, then at laboratory temperature for 30 minutes, and was then evaporated to dryness. Water (1 ml.), diethyl ether (2 ml.) and acetic acid (0.01 ml.) were added and the mixture was kept at laboratory temperature for 12 hours and then evaporated to dryness. The residue was purified by chromatography on a silica gel column using toluene as eluant and there was thus obtained benzyl 5-methyl-2-oxohexanoate as an oil.

Ethyl 6,6-(2,2-dimethyltrimethylene-1,3-dioxy)-2-oxo-6-phenylhexanoate (Note 4)

A solution of 3-chloropropyl phenyl ketone (23 g.), 2,2-dimethylpropane-1,3-diol (66 g.) and p-toluenesulphonic acid (0.5 g.) in benzene (300 ml.) was heated under reflux for 12 hours in a Dean and Stark water-separating apparatus, cooled and filtered. The filtrate was poured onto a silica gel column which was then eluted with toluene. The eluate was evaporated to dryness and there was thus obtained 2-(3-chloropropyl)-5,5-dimethyl-2-phenyl-1,3-dioxan.

The above compound (37 g.) was added to a solution of sodium cyanide (7.35 g.) in dimethyl sulphoxide (100 ml.) which was heated at 80° C., and the mixture was heated at 95° C. for 6 hours, cooled and poured into water (500 ml.). The mixture was extracted three times with diethyl ether (100 ml. each time) and the combined extracts were washed with water, dried over magnesium sulphate and evaporated to dryness.

Methyl methylthiomethyl sulphoxide (16.6 ml.) was added slowly to a stirred suspension of sodium hydride (7.9 g. of a 50% dispersion in oil from which the oil had been removed by washing with petroleum ether b.p. 60°–80° C.) in tetrahydrofuran (160 ml.) and the mixture was stirred at laboratory temperature for 30 minutes. A solution of the 2-(3-cyanopropyl)-5,5-dimethyl-2-phenyl-1,3-dioxan obtained as described in the previous paragraph (28.4 g.) in tetrahydrofuran (30 ml.) was added and the mixture was stirred at 60° C. for 16 hours and then cooled. Water (6 ml.) was added dropwise, and the mixture was diluted with dichloromethane (800 ml.), dried over magnesium sulphate and evaporated to dryness. The residue was purified by medium pressure liquid chromatography on a silica gel column using a 50:1 v/v mixture of dichloromethane and methanol as eluant. There was thus obtained 1-[4,4-(2,2-dimethyltrimethylene-1,3-dioxy)-4-phenylbutyl]-2-methylsulphinyl-2-methylthioetheneamine.

Cupric chloride dihydrate (12.0 g.) and cupric oxide (19.0 g.) were added to a stirred solution of the above amine (23.7 g.) in ethanol (300 ml.) and the mixture was stirred at laboratory temperature for 18 hours. Further cupric chloride dihydrate (6.0 g.) and cupric oxide (9.5 g.) were added and the mixture was stirred for a further 24 hours and then filtered and the filtrate was evaporated to dryness under reduced pressure. Dichloromethane (600 ml.) was added, the mixture was filtered through a filter-aid and the filtrate was evaporated to dryness. The residue was purified by flash chromatography on a silica gel column using dichloromethane as eluant, and there was thus obtained as an oil ethyl 6,6-(2,2-dimethyltrimethylene-1,3-dioxy)-2-oxo-6-phenylhexanoate.

Ethyl 6,6-(2,2-dimethyltrimethylene-1,3-dioxy)-2-oxo-6-(2-thienyl)hexanoate (Note 5)

A mixture of 2-(4-chlorobutyryl)thiophene (90 g.), 2,2-dimethylpropane-1,3-diol (250 g.), p-toluenesulphonic acid (10 g.) and benzene (1200 ml.) was heated under reflux for 40 hours in a Dean and Stark water-separating apparatus, cooled in an ice-bath and filtered to remove the excess of diol. Saturated aqueous sodium bicarbonate solution (100 ml.) was added, the mixture was shaken and the benzene layer was separated, dried over magnesium sulphate and evaporated to dryness under reduced pressure. The residue was purified by chromatography on a silica gel column using a 1:1 v/v mixture of hexane and dichloromethane as eluant.

A Grignard reagent was prepared during 30 minutes by conventional means from a solution of the 2-[4-chloro-1,2-(2,2-dimethyltrimethylene-1,3-dioxy)-butyl]thiophen thus obtained (7.25 g.) in tetrahydrofuran (10 ml.) and magnesium turnings (0.64 g.) under an atmosphere of argon, and the mixture was heated under reflux for 3 hours. Additional tetrahydrofuran (30 ml.) was added, and the Grignard reagent ws added dropwise during 30 minutes to a stirred solution of diethyl oxalate (20.6 g.) in tetrahydrofuran (40 ml.) which was maintained at −5° C. under an atmosphere of argon. The mixture was allowed to warm up to laboratory temperature during 16 hours, quenched with saturated aqueous ammonium chloride solution and filtered. The filtrate was evaporated to dryness under reduced pressure and the residue was purified by chromatography on a silica gel column using 3:1 v/v mixture of dichloromethane and hexane as eluant. There was thus obtained ethyl 6,6-(2,2-dimethyltrimethylene-1,3-dioxy)-2-oxo-6-(2-thienyl)hexanoate.

Ethyl 6-(benzo[b]fur-2-yl-6,6-(2,2-dimethyltrimethylene-1,3-dioxy)-2-oxo-hexanoate (Note 6)

A mixture of salicyclaldehyde (122 g.), 2,2-diethoxyethyl bromide (216 g.), potassium carbonate (152 g.) and dimethylformamide (500 ml.) was heated under reflux for 90 minutes, cooled and filtered and the filtrate was evaporated to dryness under reduced pressure. The residue was partitioned between ethyl acetate and water and the organic layer was dried and evaporated to dryness. The residue was distilled under reduced pressure and there was thus obtained 2-(2,2-diethoxyethoxy)benzaldehyde, b.p. 135°–138° C./0.4 mm.Hg.

A solution of the above compound (168 g.) in acetic acid (420 ml.) was heated under reflux for 20 hours, the acetic acid was removed by evaporation under reduced pressure and the residue was distilled under reduced pressure. There was thus obtained benzo[b]furan-2-carboxaldehyde, b.p. 92°–9520 C./0.5 mm.Hg.

The above aldehyde (7.3 g.) was added dropwise during 5 minutes to a stirred mixture of trimethylsilyl cyanide (4.95 g.) and zinc iodide (0.004 g.) which was kept at laboratory temperature by cooling with a water bath, and the mixture was stirred at laboratory temperature for 1 hour, at 90° C. for 15 minutes and then distilled over a short path at 0.1 mm.Hg. pressure, bath temperature 100° C.

A solution of the 2-(benzo[b]-fur-2-yl)-2-trimethylsilyloxyacetonitrile thus obtained (9.8 g.) in tetrahydrofuran (25 ml.) was added during 5 minutes to a stirred solution of lithium diisopropylamide [prepared at 0° C. in tetrahydrofuran solution (120 ml.) from diisopropylamine (4.0 g.) and n-butyl-lithium (28.6 ml. of 1.4 molar solution in hexane)] in tetrahydrofuran (120 ml.) which was cooled to −78° C. under an atmosphere of nitrogen, and the mixture was stirred at that temperature for 15 minutes. 4-Bromobutyronitrile (5.9 g.) was added and the mixture was stirred at −78° C. for 30 minutes, then at 0° C. for 30 minutes and finally at laboratory temperature for 1 hour. The tetrahydrofuran was removed by evaporation under reduced pressure and the residue was partitioned between ethyl acetate and water. The ethyl acetate layer was separated, washed with saturated aqueous sodium chloride solution, dried and evaporated to dryness. A mixture of a solution of the residue in methanol (400 ml.) and aqueous 4N-hydrochloric acid (40 ml.) was stirred at laboratory temperature for 2 hours, aqueous 4N-ammonium hydroxide solution (80 ml.) was added and the mixture was stirred at laboratory temperature for 1 hour. The methanol was removed by evaporation under reduced pressure and the aqueous residue was filtered. The solid product was crystallised from methanol and there was thus obtained 1-(benzo[b]fur-2-yl)-4-cyanobutan-1-one, m.p. 79° C.

This compound was reacted with 2,2-dimethylpropane-1,3-diol as described under Note 4 above, and the dioxan thus obtained was converted to ethyl 6-(benzo[b]fur-2-yl)-6,6-(2,2-dimethyltrimethylene-1,3-dioxy)-2-oxohexanoate by reaction with dimsyl sodium also as described under Note 4 above.

EXAMPLE 5

A mixture of N-(1-ethoxycarbonyl-3-phenylpropyl)-L-alanyl-L-proline methanesulphonamide (Example 1; 0.3 g.), ethanol (30 ml.) and aqueous N-sodium hydroxide solution (30 ml.) was stirred at laboratory temperature for 30 minutes, neutralised with aqueous N-hydrochloric acid (30 ml.) and evaporated to dryness under reduced pressure. Last traces of water were removed by azeotroping with toluene, and the residue was stirred with ethanol. The mixture was filtered, the filtrate was evaporated to dryness under reduced pressure and the residue was purified by chromatography on a silica gel column using a 10:4:1 v/v/v mixture of chloroform, methanol and water as eluant. There was thus obtained N-(1-carboxy-3-phenylpropyl)-L-alanyl-L-proline methanesulphonamide as a white powder.

The process described above was repeated using a 1-ethoxycarbonyl compound described in Example 2, 3 or 4 as starting material and there were thus obtained the compounds described in the following table:

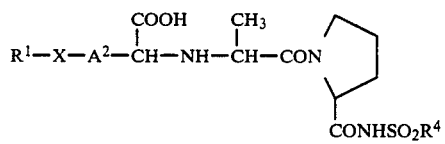

| $R^1$ | X | $A^2$ | $R^4$ | Note |
|---|---|---|---|---|
| phenyl | $CH_2$ | $CH_2$ | ethyl | 1 |
| phenyl | $CH_2$ | $CH_2$ | n-butyl | |
| phenyl | $CH_2$ | $CH_2$ | phenyl | |
| phenyl | $CH_2$ | $CH_2$ | benzyl | |
| benzo[b]fur-2-yl | $X^1$ | $(CH_2)_3$ | ethyl | 2 |
| benzo[b]fur-2-yl | CO | $(CH_2)_3$ | ethyl | |

Note 1 Each separate isomer (Example 2) was hydrolysed and the acid was purified by chromatography on a silica gel column using an 11:8:2 v/v/v mixture of methylene chloride, methanol and water. N—[(1R or S)—1-carboxy-3-phenylpropyl)-L-alanyl-L-proline ethanesulphonamide (the more active, as an inhibitor of ACE, isomer) had m.p. 156–160° C.

Note 2 $X^1$ has the meaning stated in Example 4.

EXAMPLE 6

A stream of hydrogen chloride was passed slowly for 15 minutes through a stirred solution of N-[(1 R or S)-1-carboxy-3-phenylpropyl]-L-alanyl-L-proline ethanesulphonamide (Example 5); 0.3 g.) in n-butanol (10 ml.) which was cooled to 10° C., and the mixture was kept at laboratory temperature for 4 days and then evaporated to dryness under reduced pressure. The residue was partitioned between aqueous 10% sodium carbonate solution and diethyl ether and the aqueous layer was separated, washed with diethyl ether, acidified to pH 4 with aqueous citric acid solution and extracted three times with ethyl acetate. The combined extracts were dried and evaporated to dryness and the residue was purified by chromatography on a silica gel column using a 97:3 v/v mixture of ethyl acetate and acetic acid as eluant. There was thus obtained as an oil N-[(1 R or S)-1-n-butoxycarbonyl-3-phenylpropyl]-L-alanyl-L-proline ethanesulphonamide.

N-[(1 R or S)-1-isopropoxycarbonyl-3-phenylpropyl]-L-alanyl-L-proline ethanesulphonamide was similarly obtained using isopropanol instead of n-butanol.

EXAMPLE 7

The process described in Example 1 was repeated using (gamma-t-butyl-alpha-L-glutamyl)-L-proline ethanesulphonamide as starting material in place of L-alanyl-L-proline methanesulphonamide trifluoroacetate. There was thus obtained as an oil N-[(1 RS)-1-ethoxycarbonyl-3-phenylpropyl]-(gamma-t-butyl-alpha-L-glutamyl)-L-proline ethanesulphonamide, the structure of which was confirmed by proton magnetic resonance and mass spectroscopy.

The (gamma-t-butyl-alpha-L-glutamyl)-L-proline ethanesulphonamide used as starting material was prepared by the reaction of N-benzyloxycarbonyl-gamma-t-butyl-L-glutamic acid alpha-2,4,5-trichlorophenyl ester and L-proline ethanesulphonamide by a similar process to that described in the last part of Example 3. A solution of the benzyloxycarbonyl compound thus obtained (3.0 g.) in methanol (20 ml.) was added to a stirred suspension of a 10% palladium-on-charcoal catalyst (0.6 g.) in acetic acid (20 ml.) at 5° C., sodium formate (1.2 g.) was added portionwise and the mixture was stirred at laboratory temperature for 30 minutes and then filtered. The filtrate was evaporated to dryness and the residual (gamma-t-butyl-alpha-L-glutamyl)-L- proline ethylsulphonamide was used without further purification.

EXAMPLE 8

A mixture of N-[(1 RS)-1-ethoxycarbonyl-3-phenylpropyl] -(gamma-t-butyl-alpha-L-glutamyl)-L-proline ethanesulphonamide (Example 7; 1.3 g.) and trifluoroacetic acid (5 ml.) was stirred at laboratory temperature for 150 minutes. The excess of trifluoroacetic acid was removed by evaporation and toluene was twice added and removed by evaporation. There was thus obtained as residual oil N-[(1 RS)-1-ethoxycarbonyl-3-phenylpropyl]-alpha-L-glutamyl-L-proline ethylsulphonamide trifluoroacetate.

EXAMPLE 9

The process described in Example 1 was repeated except that $N^6$-t-butyloxycarbonyl-L-lysyl-L-proline methanesulphonamide was used as starting material in place of L-alanyl-L-proline methanesulphonamide trifluoroacetate. There was thus obtained as an oil $N^6$-t-butoxycarbonyl-$N^2$-[(1 RS)-1-ethoxycarbonyl-3-phenylpropyl]-L-lysyl-L-proline methanesulphonamide, the structure of which was confirmed by proton magnetic resonance and mass spectroscopy.

The above compound was treated with trifluoroacetic acid by a similar process to that described in the last paragraph of Example 1, and there was thus obtined $N^2$-[(1 RS)-1-ethoxycarbonyl-3-phenylpropyl]-L-lysyl-L-proline methanesulphonamide bis-trifluoroacetate.

The $N^6$-t-butoxycarbonyl-L-lysyl-L-proline methanesulphonamide used as starting material was obtained from $N^2$-benzyloxycarbonyl-$N^6$-t-butoxycarbonyl-L-lysine 2,4,5-trichlorophenyl ester and L-proline methanesulphonamide, followed by removal of the benzyloxycarbonyl group, by a similar process to that described in the second part of Example 7.

EXAMPLE 10

The process described in Exaple 1 was repeated except that $N^6$-benzyloxycarbonyl-L-lysyl-L-proline methanesulphonamide trifluoroacetate was used as starting material in place of L-alanyl-L-proline methanesulphonamide trifluoroacetate. The $N^6$-benzyloxycarbonyl-$N^2$-[(1 RS)-1-ethoxycarbonyl-3-phenylpropyl]-L-lysyl-L-proline methanesulphonamide thus obtained was hydrolysed with sodium hydroxide by a similar process to that described in Example 5, and the $N^6$-benzyloxycarbonyl-$N^2$-[(1 RS)-1-carboxy-3-phenylpropyl]-L-lysyl-L-proline methanesulphonamide thus obtained (a white solid purified by chromatography on a silica gel column using an 11:8:2 v/v/v mixture of methylene chloride, methanol and water) was hydrogenolysed with hydrogen and a 10% palladium-on-charcoal catalyst by a similar process to that decribed in the second paragraph of Example 1. There was thus obtained as an oil $N^2$-[(1 RS)-1-carboxy-3-phenylpropyl]-L-lysyl-L-proline methanesulphonamide, the structure of which was confirmed by proton magnetic resonance and mass spectroscopy.

The $N^6$-benzyloxycarbonyl-L-lysyl-L-proline methanesulphonamide used as starting material was obtained from $N^6$-benzyloxycarbonyl-$N^2$-t-butoxycarbonyl-L-lysine 2,4,5-trichlorophenyl ester and L-proline methanesulphonamide by a similar process to that described in the last part of Example 3, and the t-butoxycarbonyl group was removed with trifluoroacetic acid by a similar process to that described in the last part of Example 1. There was thus obtained $N^6$-benzyloxycarbonyl-L-lysyl-L-proline methanesulphonamide trifluoroacetate.

What we claim is:

1. An amide derivative of the formula:

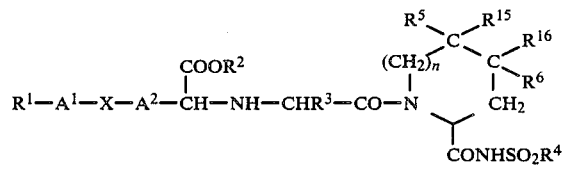

wherein either $R^1$ is aryl or heterocyclic and $A^1$ is a direct link, or $R^1$ is aryl or heterocyclic, or hydrogen or amino and $A_1$ is alkylene of 1 to 5 carbon atoms; wherein X is —CO— or has the formula

wherein $R^{11}$ and $R^{12}$, which may be the same or different, each is alkyl of up to 5 carbon atoms, or $R^{11}$ and $R^{12}$ are joined to form alkylene of 2 to 5 carbon atoms; wherein $A^2$ is alkylene of 2 to 4 carbon atoms; wherein $R^2$ is hydrogen, aryl or alkyl of up to 5 carbon atoms which is unsubstituted or which bears an aryl substituent; wherein $R^3$ is hydrogen or alkyl of up to 5 carbon atoms which is unsubstituted or which bears a halogeno, hydroxy, amino, guanidino, carboxy, carbamoyl or mercapto substituent, or an alkoxy, alkylamino, dialkylamino, cyclic amino or alkylthio substituent wherein each alkyl is of up to 5 carbon atoms and wherein cyclic amino has up to 6 carbon atoms, or an alkanoylamino or alkoxycarbonyl substituent each of up to 6 carbon atoms or an arylalkoxycarbonyl substituent of up to 10 carbon atoms, or an aryl or heterocyclyl substituent; wherein $R^4$ is alkyl of up to 5 carbon atoms which is unsubstituted or which bears an aryl substituent, or $R^4$ is phenyl or alkylphenyl; wherein n is 0 or 1; and wherein either $R^5$, $R^6$, $R^{15}$ and $R^{16}$ are all hydrogen, or $R^5$ and $R^6$ are both hydrogen and $R^{15}$ and $R^{16}$ together form tetramethylene [—$(CH_2)_4$—]; or $R^5$ and $R^6$ together form a second bond between the two carbon atoms to which they are attached and $R^{15}$ and $R^{16}$ together form buta-1,3-dien-1,4-diyl such that together with the $CR^5$–$CR^6$ group they form a fused benzo-ring; or a salt thereof where appropriate.

2. An amide derivative as claimed in claim 1 wherein $R^1$ is phenyl, p-methoxyphenyl, 2-thienyl or benzo[b]fur-2-yl, $A^1$ is a direct link, X is —CO— or 2,2-dimethyltrimethylene-1,3-dioxymethylene, $A^2$ is ethylene or trimethylene, $R^2$ is hydrogen, alkyl of up to 5 carbon atoms, or benzyl, $R^3$ is methyl, 4-aminobutyl, 2-carboxyethyl or 2-alkoxycarbonylethyl and the stereochemistry of —$CHR^3$— is that derived from L-alanine, L-lysine or L-glutamic acid respectively, n is 0, $R^5$, $R^6$, $R^{15}$ and $R^{16}$ are all hydrogen and $R^4$ is phenyl or alkyl of up to 5 carbon atoms which is unsubstituted or which bears a phenyl substituent.

3. An amide derivative as claimed in claim 1 wherein $R^1$ is phenyl, p-methoxyphenyl, 2-thienyl or benzo[b]fur-2-yl, $A^1$ is a direct link, X is —CO— or 2,2-dimethyltrimethylene-1,3-dioxymethylene, $A^2$ is ethylene or trimethylene, $R^2$ is hydrogen or alkyl of up to 5 carbon atoms, $R^3$ is methyl (such that $-CHR^3+$ is derived from L-alanine), n is O, $R^5$, $R^6$, $R^{15}$ and $R^{16}$ are all hydrogen and $R^4$ is alkyl of up to 5 carbon atoms.

4. A pharmaceutical composition for the treatment of hypertension or congestive heart failure comprising as active ingredient an effective amount of at least one amide derivative or a salt thereof, claimed in claim 1, in association with a pharmaceutically-acceptable diluent or carrier therefor.

5. A composition as claimed in claim 4 which is, a tablet, capsule, aqueous or oily solution or suspension, emulsion, injectable aqueous or oily solution or suspension, dispersible powder, spray or aerosol formulation.

6. A composition as claimed in claim 4 which contains, in addition to the amide derivative, one or more drugs selected from diuretics and $\beta$-adrenergic blocking agents.

7. A method for the treatment of hypertension or congestive heart failure in a warm-blooded animal in need of such treatment which comprises administering to said animal an effective amount of an amide derivative or salt thereof claimed in claim 1.

* * * * *